United States Patent [19]

Chorvat et al.

[11] 4,007,194

[45] Feb. 8, 1977

[54] PROCESS AND INTERMEDIATES FOR MANUFACTURE OF 2-AZASTEROIDS

[75] Inventors: Robert J. Chorvat, Arlington Heights; Raphael Pappo, Skokie, both of Ill.

[73] Assignee: G. D. Searle & Co., Chicago, Ill.

[22] Filed: May 6, 1974

[21] Appl. No.: 467,217

[52] U.S. Cl. .................. 260/289 AZ; 260/283 SC; 260/289 D; 260/464; 424/258

[51] Int. Cl.$^2$ ....................................... C07D 217/12

[58] Field of Search .... 260/289 AZ, 289 R, 289 C, 260/283 SC

[56] References Cited

UNITED STATES PATENTS 3,290,287 12/1966 Mazur et al. ............... 260/289 AZ
3,887,567 6/1975 Chorvat et al. ............. 260/289 AZ

OTHER PUBLICATIONS

Burger "Medicinal Chemistry" 3rd ed., part I, (1970) Wiley, N. Y. p. 662.
Chorvat et al., "Chem. Abstracts," vol. 77, 1972, Abstract 11468n of Tetrahedron Lett., 1972 (31) pp. 3237–3240.

*Primary Examiner*—Donald G. Daus
*Assistant Examiner*—D. B. Springer
*Attorney, Agent, or Firm*—John J. McDonnell

[57] ABSTRACT

2-Azasteroids, displaying valuable pharmacological properties, e.g. anti-viral, are manufactured by a total synthesis originating with dihydroresorcinol.

6 Claims, No Drawings

PROCESS AND INTERMEDIATES FOR MANUFACTURE OF 2-AZASTERIOIDS

The present invention is concerned with a novel process and novel intermediates useful in the production of 2-azasteroids, which display valuable pharmacological properties, e.g. anti-viral.

The preferred group of intermediates is represented by the tetracyclic compounds of the following structural formula

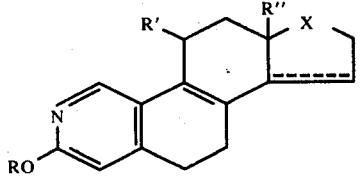

wherein R is a lower alkyl, tri-(lower alkyl)silyl or lower cycloalkyl radical, R' is hydrogen or lower alkyl and R'' is lower alkyl radicals, X is a carbonyl or a β-hydroxymethylene radical and the dotted line represents an optionally doubly-bonded linkage.

The lower alkyl radicals denoted in the foregoing structural formula are typified by methyl, ethyl, propyl, butyl, pentyl, hexyl, heptyl and the branched-chain isomers thereof.

Representative of the lower cycloalkyl radicals are cyclopentyl and cyclohexyl.

The novel intermediates of the present invention originate from a novel process which utilizes dihydro=λ resorcinol as the starting material. That substance thus is allowed to react with a chlorinating reagent such as phosphorus trichloride to afford 3-chloro-2-cyclohexen-1-one. Reaction with cyanoacetamide and sodium hydride results in α-cyano-3-oxo-1-cyclohexen-1-acetamide, which is contacted with a dialkylformamide acetal, for example dimethylformamide diethyl acetal or dimethylformamide dineopentyl acetal, to produce 2,3,5,6,7,8-hexahydro-3,8-dioxo-4-isoquinolinecarboni=trile. Elimination of the cyano group is effected by heating with hydrobromic acid, thus affording 2,3,5,6,7,8-hexahydro-3,8-isoquinolinedione. Heating with an alkyl, trialkylsilyl or cycloalkyl halide produces the corresponding 6-alkoxy, 6-trialkylsilyloxy and 6-cycloalkoxy 7-aza-1-tetralones together with the N-alkylated or N-cycloalkylated derivatives. Typically, 2,3,5,6,7,8-hexahydro-3,8-isoquinolinedione is heated in benzene at the reflux temperature with methyl iodide and silver carbonate to yield 7-aza-6-methoxy-1-tetra=lone together with 2-methyl-2,3,5,6,7,8-hexahydro-3,8-isoquinolinedione. The reaction of the keto group of the latter tetralone with vinyl magnesium chloride results in 7-aza-6-methoxy-1-vinyl-1-tetralol, which is contacted with a 2-(lower alkyl)cyclopentane-1,3-dione, such as 2-methylcyclopentane-1,3-dione, in the presence of a basic catalyst such as triethylamine to afford 5,6,7,8-tetrahydro-3-methoxy-8-[(2-methyl-1,3-dioxocylopent-2-yl)ethylidene]isoquinoline. Alternatively, the tetralol is converted to the iso-thiouronium salt, which is reacted with the dione to afford the latter product. Cyclization of the latter diketone, suitably in the presence of p-toluenesulfonic acid, results in dl-2-aza-3-methoxyestra-1,3,5(10), 8,14-pentaen-17-one. Catalytic hydrogenation, using a palladium-on-calcium carbonate catalyst effects saturation of the 14-double bond, thus producing dl-2-aza-3-methoxyestra-1,3,5(10),8-tetraen-17-one, while chemical reduction, for example with sodium borohydride, converts the 17-keto group, thus yielding dl-2-aza-3-methoxyestra-1,3,5(10),8,14-pentaen-17β-ol. The 14-double bond of the latter substance is catalytically reduced, using a palladium-on-calcium carbonate catalyst, to yield dl-2-aza-3-methoxy=estra-1,3,5(10),8-tetraen-17β-ol, which is allowed to react with sodium in liquid ammonia to afford dl-2-aza-3-methoxyestra-1,3,5(10)-trien-17β-ol.

The 11β-alkyl compounds of the present invention are produced by reacting a 1-alkylvinyl organometallic reagent with the aforementioned 7-aza-6-oxygenated-1-tetralones and subjecting the resulting tetralols to the successive processes described hereinbefore. Suitable organometallic reagents are typified by 1-alkylvinyl magnesium halides and 1-alkylvinyl lithiums. As a specific example, the aforementioned 7-aza-6-methoxy-1-tetralone is contacted with 1-methylvinyl magnesium chloride to afford 7-aza-6-methoxy-1-(1-methylvinyl)-1-tetralol.

The 2-azaestratrienes, as typified by the aforementioned dl-2-aza-3-methoxyestra-1,3,5(10)-trien-17β-ol, are valuable pharmacological agents as is evidenced by their anti-viral activity. A suitable assay for detection of that activity is described as follows:

Cell cultures of primary Rhesus monkey kidney maintained in 25 cc. plastic flasks and each containing test compound in concentrations of 625, 125, 25, 5, or 1 μg./ml are prepared in pairs. These flasks and an identical pair of flasks containing no test compound are each inoculated with a dose of influenza virus type A (Strain 575) previously shown to produce maximum hemadsorption and minimum cytopathogenic effects after a 24-hour incubation. Where the cultures contain test compound the viruses are added 1 hour after addition of the test compound to the culture. After 24 hour incubation of the cultures the supernatant fluids are removed and 3.0 ml. of a 0.4% suspension of guinea pig erythrocytes is added to each flask. The flasks are then incubated at 4° C. in a horizontal position for 30 minutes. The flasks are rocked every 10 minutes during the incubation period. After this incubation the red cell suspension is decanted from each flask. The flasks are washed twice with 3.0 ml. of phosphate buffer solution (pH 7.4) to remove unabsorbed red cells and 3.0 ml. of distilled water is then added to lyse the absorbed cells. The flasks are then further incubated at 37° C. for 30 minutes in a horizontal position and the flasks are rocked every 10 minutes. After this incubation the fluid contents of the pairs of flasks are combined to form an assay unit and are placed at room temperature for 15–30 minutes to allow settling of the cellular debris. A pair of control flasks identical with the above except for the absence of the test compound and virus inoculation are run concurrently. The resulting hemoglobin solutions from each assay unit are then read for optical density in a Beckman spectrophotometer at about 415 mμ. A test compound is considered active if at any one of the tested levels it reduces the optical density reading by at least 50% relative to the virus control.

The invention will appear more fully from the examples which follow. These examples are given by way of illustration only and are not to be construed as limiting the invention either in spirit or in scope as many modifications both in materials and methods will be apparent to those skilled in the art. In these examples temperatures are given in degrees Centigrade and quantities of materials in parts by weight unless otherwise noted.

EXAMPLE 1

To a solution of 400 parts of dihydroresorcinol in 2000 parts by volume of chloroform is added 161.2 parts of phosphorus trichloride and the resulting reaction mixture is stirred and heated at the reflux temperature in a nitrogen atmosphere for about 3¼ hours. The mixture is then cooled and poured carefully into approximately 1000 parts of a mixture of ice and water. The layers are separated and the aqueous phase is extracted with ether. The ether extracts are combined with the chloroform layer and the resulting organic solution is washed successively with 5% aqueous sodium hydroxide and water, then dried over anhydrous sodium sulfate. Removal of the solvent by distillation under reduced pressure affords the crude product, which is purified by distillation under reduced pressure, thus affording 3-chloro-2-cyclohexen-1-one, boiling at about 65° under 3 mm. pressure. Infrared absorption maxima in chloroform are observed at about 5.93 and 6.20 microns and a nuclear magnetic resonance peak in deuterochloroform at 6.23 parts per million.

EXAMPLE 2

To a mixture of 58 parts of sodium hydride and 1800 parts by volume of ethylene glycol dimethyl ether, under nitrogen, is added, at room temperature over a period of about 30 minutes, 198 parts of cyanoacetamide. That mixture is heated at the reflux temperature for about 30 minutes, then cooled to approximately room temperature and 145.2 parts of 3-chloro-2-cyclohexen-1-one is added over a period of about 15 minutes. The mixture is stirred and heated at the reflux temperature for about 1 hour, then is cooled and a solution consisting of 20 parts by volume of methanol and 10 parts by volume of water is cautiously added dropwise. An additional 500 parts of water is then added and the organic solvents are removed by distillation under reduced pressure. Acidification of the residual aqueous solution to pH 1–2 results in precipitation of the product, which is isolated by filtration, then washed with cold water and dried. Purification of that crude product is effected by recrystallization from ethanol-water-ethyl acetate, thus affording $\alpha$-cyano-3-oxo-1-cyclohexen-1-acetamide, melting at about 181°–830°. This compound exhibits an ultraviolet absorption maxima, in methanol, at about 370 m$\mu$ with a molecular extinction coefficient of about 21,900, infrared absorption peaks, in potassium bromide, at about 2.97, 4.55 and 6.02 microns and nuclear magnetic resonance maxima, in deuteropyridine, at about 1.73, 2.41 and 2.93 parts per million.

EXAMPLE 3

To a solution consisting of 40 parts of $\alpha$-cyano-3-oxo-1-cyclohexen-1-acetamide in 125 parts by volume of dimethylformamide, in an atmosphere of nitrogen, is added dropwise, over a period of 10–15 minutes, 40 parts of dimethylformamide diethyl acetal. After the reaction mixture is stirred at room temperature for about 18 hours, 10 parts of water is added and the organic solvents are removed by distillation under reduced pressure. The residual oily product is extracted with dilute aqueous sodium hydroxide and the extract is washed several times with chloroform, then filtered to remove he small amount of insoluble material. Neutralization of the alkaline solution by the addition of dilute hydrochloric acid results in precipitation of the product, which is purified by recrystallization from aqueous acetone to afford 2,3,5,6,7,8-hexahydro-3,8-dioxo-4-isoquinolinecarbonitrile, melting above 290°. It is further characterized by ultraviolet absorption maxima at about 227, 232, 279 and 324 m$\mu$ with molecular extinction coefficients of 17,900, 16,000, 13,000 and 6,800, respectively, and by infrared absorption peaks, in potassium bromide, at about 2.87, 2.97, 4.48, 5.92, 6.03, 6.07, 6.23 and 6.45 $\mu$ and also by nuclear magnetic resonance peaks, in deutero-pyridine, at approximately 1.92, 2.58, 2.97, and 8.72 parts per million.

EXAMPLE 4

A solution of 28.4 parts of 2,3,5,6,7,8-hexahydro-3,8-dioxo-4-4-isoquinolinecarbonitrile in 500 parts by volume of 48% hydrobromic acid is heated at the reflux temperature in the absence of light for about 7 hours, following which time the solvent is removed by distillation under reduced pressure. The resulting residue is partitioned between chloroform and aqueous sodium chloride and the layers are separated. The aqueous phase is extracted several times with chloroform, then combined with the original chloroform layer. That organic solution is washed with aqueous sodium chloride, then dried over anhydrous sodium sulfate and stripped of solvent under reduced pressure to afford the crude product. The original aqueous layer is neutralized by the addition of sodium bicarbonate, then is extracted with chloroform. Evaporation of that chloroform extract to dryness affords additional product. The combined crude product is purified by recrystallization from aqueous acetone, thus affording pure 2,3,5,6,7,8-hexahydro-3,8-isoquinolinedione, melting at about 246°–248° with decomposition. Ultraviolet absorption maxima are observed in methanol at 279 and 221 m$\mu$ with molecular extinction coefficients of about 16,700 and 13,500, respectively. In deuteropyridine, nuclear magnetic resonance peaks are displayed at about 1.96, 2.57, 2.92, 5.50 and 8.71 parts per million.

EXAMPLE 5

To a solution of 2.6 parts of 2,3,5,6,7,8-hexahydro-3,8-isoquinolinedione in 375 parts by volume of dry benzene is added 2.3 parts of silver carbonate and 5 parts by volume of methyl iodide and the resulting mixture is heated at the reflux temperature in the absence of light under an atmosphere of nitrogen for about 4 hours. At the end of that time the mixture is cooled and filtered through diatomaceous earth to afford an organic solution, which is extracted several times with 6 N hydrochloric acid. Those acidic extracts are washed with chloroform, then made alkaline by the addition of aqueous sodium hydroxide and extracted with ether. The ether extracts are combined and washed with saturated aqueous sodium chloride, then dried over anhydrous sodium sulfate and stripped of solvent under reduced pressure. The resulting crude product is purified by recrystallization from water to yield 7-aza-6-methoxy-1-tetralone, melting at about 55.5°–57°. This compound displays an ultraviolet absorption maximum at about 268 m$\mu$ with a molecular extinction coefficient of about 13,100, infrared absorption peaks, in chloroform, at about 5.92, 6.23, and 7.80 $\mu$ and nuclear magnetic resonance maxima, in deuterochloroform, at about 2.14, 2.64, 2.91, 3.97, 6.56 and 8.83 parts per million.

The aforementioned chloroform washings are evaporated to dryness under reduced pressure and the residual oil is extracted with benzene. The resulting organic solution is diluted with hexane to the point of incipient trubidity, then is decolorized with activated carbon. The decolorized solution is diluted with hexane, then cooled, thus affording crystalline 2-methyl-2,3,5,6,7,8-hexahydro-3,8-isoquinolinedione, melting at about 94°–97°. It is characterized further by ultraviolet absorption maxima, in methanol, at about 224 and 281 m$\mu$ with molecular extinction coefficients of about 14,500 and 16,100, respectively, by infrared absorption maxima, in chloroform, at about 5.88 and 6.05 $\mu$0 and by nuclear magnetic resonance peaks, in deuterochloroform, at about 2.10, 2.59, 2.84, 3.63, 6.35 and 8.28 parts per million.

EXAMPLE 6

To a solution of 10 parts of 7-aza-6-methoxy-1-tetralone in 140 parts by volume of xylene, in a nitrogen atmosphere, is added dropwise, at -20° over a period of about 45 minutes, 45 parts by volume of 2.84 M vinyl magnesium chloride in tetrahydrofuran dissolved in 60 parts by volume of xylene. The resulting reaction mixture is stirred between −15° and −20° for about 90 minutes, then is diluted with approximately 100 parts by volume of saturated aqueous ammonium chloride. That diluted mixture is allowed to warm to room temperature, at which time the layers are separated and the aqueous phase is extracted with ether. The combined organic extracts are washed successively with aqueous ammonium chloride and saturated aqueous sodium chloride, then dried over anhydrous sodium sulfate. To that organic solution containing 7-aza-6-methoxy-1-vinyl-1-tetralol is added 6.9 parts of 2-methylcyclopentane-1,3-dione and 5.8 parts of triethylamine and that reaction mixture is partially concentrated to remove the ether and tetra=hydrofuran, then is heated at the reflux temperature under nitrogen, during which time the water of reaction is removed by means of a water trap. That mixture is then cooled and extracted with dilute aqueous sodium hydroxide. The layers are separated and the aqueous layer is extracted with benzene. The organic solutions are combined, washed with saturated aqueous sodium chloride, dried over anhydrous sodium sulfate, decolorized with activated carbon, then filtered. Removal of the solvent by distillation under reduced pressure affords an oily residue, which is purified by crystallization from ether, thus affording 5,6,7,8-tetrahydro-3-methoxy-8-[(2-methyl-1,3-dioxocyclopent-2-yl)ethylidene]isoquin=oline, melting at about 79°–80.5° and displaying an ultraviolet absorption maximum at 262 millimicrons with a molecular extinction coefficient of 18,000, infrared absorption peaks, in chloroform at 5.78, 6.20 and 6.73 microns and nuclear magnetic resonance peaks, in deutero=λ chloroform, at 1.17, 2.73, 3.92, 5.72, 6.44 and 8.25 parts per million.

EXAMPLE 7

To a solution of 15 parts of p-toluenesulfonic acid monohydrate in 750 parts by volume of dioxane is added a solution of 8.75 parts of 5,6,7,8-tetrahydro-3-methoxy-8-[(2-methyl-1,3-dioxocyclopent-2-yl)ethyliden]=isoquinoline in 1500 parts by volume of xylene and the resulting reaction mixture is heated at the reflux temperature under nitrogen for about 3 hours. That mixture is then cooled and 200 parts by volume of dilute aqueous sodium bicarbonate is added. The organic layer is separated and washed several times with saturated aqueous sodium chloride, then dried over anhydrous sodium sulfate and stripped of solvent by distillation under reduced pressure. The resulting deep red oily residue is triturated with acetone to yield the desired product. Further purification is effected by recrystallization from acetone, thus affording dl-2-aza-3-methoxyestra-1,3,5(10),8,14-pentaen-17-one, melting at about 167°–169° with decomposition. This compound is characterized further by an ultraviolet absorption maximum, in methanol, at about 298 m$\mu$ with a molecular extinction coefficient of about 28,000 and by nuclear magnetic resonance peaks, in deuterochloroform, at about 1.14, 3.93, 5.89, 6.55 and 8.08 parts per million.

EXAMPLE 8

To a solution of 3.75 parts of dl-2-aza-3-methoxyestra-1,3,5(10),8,14-pentaen-17-one in 125 parts by volume of methanol is added portionwise at room temperature 1.4 parts of sodium borohydride. After completion of the addition, the reaction mixture is stirred for several minutes, then is quenched by the addition of acetone. Concentration of the solution to approximately one-half volume is followed by the addition of a small amount of water and cooling, thus effecting precipitation of yellow plate-like crystals. That crude product is purified by recrystallization from aqueous acetone to yield dl-2-aza-3-methoxyestra-1,3,5(10),8,14-pentaen-17$\beta$-ol, melting at about 130°–136°. This compound exhibits an ultraviolet absorption maximum in methanol at about 300 m$\mu$ with a molecular extinction coefficient of about 28,000 and nuclear magnetic resonance peaks, in deuterochloroform, at about 1.00, 3.93, 5.56, 6.57 and 8.10 parts per million.

EXAMPLE 9

A mixture consisting of 0.678 part of dl-2-aza-3-methoxyestra-1,3,5(10),8,14-pentaen-17-one, 100 parts by volume of benzene and 0.14 part of 5% palladium-on-calcium carbonate catalyst is stirred in a hydrogen atmosphere at room temperature and atmospheric pressure until one molecular equivalent of hydrogen has been absorbed. The reaction mixture is then filtered to remove the catalyst and the filtrate is concentrated to dryness to afford the crude product. Recrystallization of that material from methanol affords pure dl-2-aza-3-methoxyestra-1,3,5(10),8-tetraen-17-one, melting at about 146°–149.5° and displaying an ultraviolet absorption maximum at about 267 m$\mu$ with a molecular extinction coeffecient of about 18,000. Nuclear magnetic resonance peaks are observed, in deuterochloroform, at about 0.90, 3.92, 6.57, and 7.97 parts per million.

EXMPLE 10

To a solution of 3.85 parts of dl-2-aza-3-methoxyestra-1,3,5(10),8,14-pentaen-17$\beta$-ol in 150 parts by volume of benzene is added 1.5 parts of 5% palladium-on-calcium carbonate catalyst and that mixture is shaken with hydrogen until one molecular equivalent of hydrogen has been absorbed. Removal of the catalyst by filtration followed by partial concentration of the filtrate and cooling results in crystallization of the product, which is isolated by filtration to afford dl-2-aza-3-methoxy=estra-1,3,5(10),8-pentaen-17β-ol, melting at about 155°-157.5°. An ultraviolet absorption maximum is observed in methanol at about 267 mμ with a molecular extinction coefficient of about 18,000 and nuclear magnetic resonance peaks, in deuterochloroform, at about 0.79, 3.93, 6.52, and 7.97 parts per million.

EXAMPLE 11

A solution of 0.4 part of dl-2-aza-3-methoxy=estra-1,3,5(10),8-tetraen-17β-ol in 25 parts by volume of tetrahydrofuran is added to approximately 40 parts by volume of ammonia, at about −70° in an atmosphere of nitrogen. To that mixture is then added 0.4 part of sodium metal and the resulting mixture is stirred for about 1 hour, at the end of which time an additional 0.15 part of sodium metal is added. Stirring is continued for approximately 45 minutes, at the end of which time approximately 4 parts of ammonium chloride is added and the mixture is allowed to warm to room temperature. Extraction with ether affords an organic solution, which is stripped of solvent under reduced pressure to afford an oily residue, consisting of a mixture of dl-2-aza-3-methoxyestra-1,3,5(10)-trien-17β-ol and dl-2-aza-3-methoxyestra-2,5(10)-dien-17β-ol. That residue is dissolved in a mixture consisting of 20 parts by volume of benzene and 10 parts by volume of acetone and the solution is cooled to approximately −10° at which time 0.32 part of dichlorodicyanobenzoquinone is added portionwise. The temperature is allowed to warm to about 10° for about 40 minutes and 10% aqueous sodium bisulfite is then added. The mixture is stirred, the layers separated and the aqueous phase extracted with ether. The combined ether extracts are washed several times with dilute aqueous sodium hydroxide, then with aqueous sodium chloride. After drying of that solution over anhydrous sodium sulfate, the solution is diluted with hexane, then filtered through diatomaceous earth. Removal of the solvent under reduced pressure affords an oil, which is triturated with methanol to yield the crude product. Recrystallization from methanol affords dl-2-aza-3-methoxyestra-1,3,5(10)-trien-17β-ol, melting at about 153°-156°. This compound is characterized by an ultraviolet absorption maximum in methanol at about 276 mμ with a molecular extinction coefficient of about 3700 and by nuclear magnetic resonance peaks in deuterochloroform at about 0.78, 3.90, 6.44 and 8.03 parts per million.

EXAMPLE 12

The substitution of an equivalent quantity of ethyl iodide in the procedure of Example 5 results in 7-aza-6-ethoxy-1-tetralone, which when substituted in the subsequent procedures described in Examples 6-11 affords 7-aza-6-ethoxy-1-vinyl-1-tetralol; 5,6,7,8-tetrahydro-3-ethoxy-8-[(2-methyl-1,3-dioxocyclopent-2-yl)ethylidene]=isoquinoline; dl-2-aza-3-ethoxyestra-1,3,5(10),8,14-pentaen-17-one; dl-2-aza-3-ethoxyestra-1,3,5(10),8,14-pentaen-17β-ol; dl-2-aza-3-ethoxyestra-1,3,5(10),8-tetraen-17-one; dl-2-aza-3-ethoxyestra-1,3,5(10),8-tetraen-17βol; and dl-2-aza-3-ethoxyestra-1,3,5(10)-trien-17β-ol.

EXAMPLE 13

When an equivalent quantity of cyclopentyl iodide is substituted in the procedure of Example 5, there is produced 7-aza-6-cyclopentyloxy-1-tetralone. The substitution of that compound in the successive processes of Examples 6-11 results in 7-aza-6-cyclopentyloxy-1-vinyl-1-tetralol; 5,6,7,8-tetrahydro-3-cyclopentyloxy-8-[(2-methyl-1,3-dioxocyclopent-2-yl)ethylidene]isoquino=line; dl-2-aza-3-cyclopentyloxyestra-1,3,5(10),8,14-pentaen-17-one; dl-2-aza-3-cyclopentyloxyestra-1,3,5(10),8,14-pentaen-17β-ol; dl-2-aza-3-cyclopentyl=oxyestra-1,3,5(10),8-tetraen-17-one; dl-2-aza-3-cyclo=pentyloxyestra-1,3,5(10),8-tetraen-17β-ol; and 2-aza-3-cyclopentyloxyestra-1,3,5(10)-trien-17β;ol.

EXAMPLE 14

To a solution of 1 part of 7-aza-6-methoxy-1-vinyl-1-tetralol in 20 parts by volume of acetic acid is added 0.4 part of thiourea and the resulting reaction mixture is warmed to achieve homogeneity. Removal of the solvent by distillation under reduced pressure affords 5,6,7,8-tetrahydro-3-methoxyisoquinolin-8-ethylideniso=thiouronium acetate.

To a solution containing 1 part of 5,6,7,8-tetrahydro-3-methoxyisoquinolin-8-ethylidenisothiouronium acetate in 20 parts by volume of 50% aqueous ethanol is added a solution of 0.5 part of 2-methylcyclopentane-1,3-dione in 5 parts of ethanol and that mixture is heated at the reflux temperature for about 1 hour, the cooled and diluted with water to effect precipitation of the product, which is isolated by filtration and dried, thus affording 5,6,7,8-tetrahydro-3-methoxy-8-[(2-methyl-1,3-dioxocyclopent-2-yl)ethyliden]isoquinoline, identical with the product of Example 6.

EXAMPLE 15

To 50 parts by volume of liquid ammonia, at about −78° in a nitrogen atmosphere, is added successively 30 parts by volume of tetrahydrofuran and sufficient sodium metal to produce a blue color in the solution. At that time an additional 0.4 part of sodium metal is added, the mixture is stirred for about 15 minutes and 0.48 part of dl-2-aza-3-methoxyestra-1,3,5(10),8-tetraen-17β-ol dissolved in 10 parts by volume of tetrahydrofuran is added. Stirring at approximately −78° is continued for about 45 minutes and the reaction mixture is then quenched by the addition of sufficient wet ether to discharge the blue color. Most of the ammonia is allowed to evaporate and the residual mixture is diluted with ether, then filtered to remove inorganic salts. The filtrate is partially concentrated, diluted with benzene, filtered through diatomaceous earth and stripped of solvent to afford a yellow oil consisting of a mixture of dl-2-aza-3-methoxyestra-1,3,5(10)-trien-17β-ol and dl-2-aza-3-methoxyestra-2,4-dien-17β-ol. Fractional crystallization of that oil from methanol affords dl-2-aza-3-methoxyestra-2,4-dien-17β-ol, melting with decomposition at about 172°-176°, displaying an ultraviolet absorption maximum in methanol at about 297 mμ with a molecular extinction coefficient of about 15,500 and also nuclear magnetic resonance peaks in deuterochloroform at about 0.72, 3.77 and 6.44 parts per million. The mother liquors are concentrated to dryness and the residue reacted with dichlorodicyanobenzoquinone according to the procedure of Example 11, thus affording dl-2-aza-3-methoxyestra-1,3,5(10)-trien-17β-ol, identical with the product of that Example.

EXAMPLE 16

To a mixture consisting of 1 part of 2,3,5,6,7,8-hexahydro-3,8-isoquinolinedione and 1 part of tertiary-butyldimethylchlorosilane in 10 parts by volume of benzene is added dropwise 1 part of triethylamine dissolved in 5 parts by volume of dioxane. The resulting reaction mixture is stirred at room temperature for about 16 hours, then filtered to remove the precipitated triethyl=amine hydrochloride. The filter cake is washed with dioxane and the washings combined with the filtrate. Removal of the solvent by distillation under reduced pressure affords 7-aza-6-tertiary-butyldimethylsilyloxy-1-tetralone.

EXAMPLE 17

When an equivalent quantity of 7-aza-6-tertiary-butyldimethylsilyloxy-1-tetralone is subjected to the successive processes of Examples 6–11, there are produced 7-aza-6-tertiary-butyldimethylsilyloxy-1-vinyl-1-tetralol; 5,6,7,8-tetrahydro-3-tertiary-butyldimethyl=λsilyloxy-8-[(2-methyl-1,3-dioxocyclopent-2-yl)ethyliden]=isoquinoline; dl-2-aza-3-tertiary-butyldimethylsilyloxy=estra-1,3,5(10),8,14-pentaen-17one; dl-2-aza-3-tertiary-butyldimethylsilyloxyestra-1,3,5(10),8,14-pentaen-17β-ol; dl-2-aza-3-tertiary-butyldimethylsilyloxyestra-1,3,5(10),8-tetraen-17-one; dl-2-aza-3-tertiary-butyldi=methylsilyloxyestra-1,3,5(10),8-pentaen-17β-ol; and dl-2-aza-3-tertiary-butyldimethylsilyloxyestra-1,3,5(10)-trien-17β-ol.

What is claimed is:

1. A dl-compound of the formula

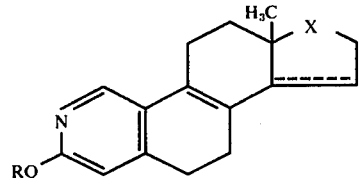

wherein R is a lower alkyl group having 1–7 carbon atoms inclusive, a tri(lower alkyl)silyl group wherein lower alkyl is a group having 1–7 carbon atoms inclusive or a lower cycloalkyl group having 5 or 6 carbon atoms, X is a carbonyl or β-hydroxymethylene group and the dotted line represents an optionally doubly-bonded linkage.

2. As in claim 1, a compound of the formula

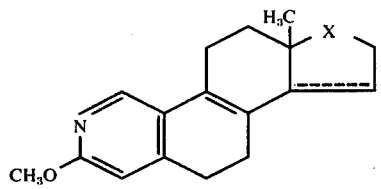

wherein X is a carbonyl or a β-hydroxymethylene group and the dotted line represents an optionally doubly-bonded linkage.

3. As in claim 1, the compound which is dl-2-aza-3-methoxyestra-1,3,5(10),8,14-pentaen-17-one.

4. As in claim 1, the compound which is dl-2-aza-3-methoxyestra-1,3,5(10),8,14-pentaen-17β-ol.

5. As in claim 1, the compound which is dl-2-aza-3-methoxyestra-1,3,5(10),8-tetraen-17-one.

6. As in claim 1, the compound which is dl-2-aza-3-methoxyestra-1,3,5(10),8-tetraen-17β-ol.

* * * * *